(12) United States Patent
Patel et al.

(10) Patent No.: US 6,916,336 B2
(45) Date of Patent: Jul. 12, 2005

(54) VASCULAR PROSTHESIS

(75) Inventors: Udayan Patel, San Jose, CA (US);
Eugene R. Serina, Union City, CA (US)

(73) Assignee: Avantec Vascular Corporation, Sunnyvale, CA (US)

(*) Notice: Subject to any disclaimer, the term of this patent is extended or adjusted under 35 U.S.C. 154(b) by 3 days.

(21) Appl. No.: 10/458,770

(22) Filed: Jun. 9, 2003

(65) Prior Publication Data

US 2004/0249446 A1 Dec. 9, 2004

(51) Int. Cl.$^7$ ................................................. A61F 2/06
(52) U.S. Cl. ..................... 623/1.16; 623/23.7; 623/1.15
(58) Field of Search .................... 623/1.1–1.2, 23.69, 623/23.7; 606/190, 194, 195, 198

(56) References Cited

U.S. PATENT DOCUMENTS

| | | | |
|---|---|---|---|
| 4,776,337 A | 10/1988 | Palmaz | |
| 5,102,417 A | 4/1992 | Palmaz | |
| 5,449,373 A | 9/1995 | Pinchasik et al. | |
| 5,697,971 A | * 12/1997 | Fischell et al. | 623/1.15 |
| 5,755,781 A | 5/1998 | Jayaraman | |
| 5,776,183 A | 7/1998 | Kanesaka | |
| 5,807,404 A | 9/1998 | Richter | |
| 5,900,754 A | * 5/1999 | Nakatani | 327/158 |
| 5,911,754 A | 6/1999 | Kanesaka et al. | |
| 5,922,020 A | 7/1999 | Klein et al. | |
| 5,922,021 A | 7/1999 | Jang | |
| 5,931,866 A | * 8/1999 | Frantzen | 623/1.15 |
| 5,954,743 A | 9/1999 | Jang | |
| 5,964,798 A | * 10/1999 | Imran | 623/1.12 |
| 5,972,018 A | 10/1999 | Israel et al. | |
| 6,013,854 A | 1/2000 | Morjuchi | |
| 6,015,429 A | 1/2000 | Lau et al. | |
| 6,017,362 A | 1/2000 | Lau | |
| 6,017,365 A | 1/2000 | Van Oepen | |
| 6,042,597 A | 3/2000 | Kveen et al. | |
| 6,068,656 A | 5/2000 | Von Oepen | |
| 6,083,259 A | * 7/2000 | Frantzen | 623/1.15 |
| 6,106,548 A | 8/2000 | Roubin et al. | |
| 6,190,403 B1 | * 2/2001 | Fischell et al. | 623/1.16 |
| 6,193,747 B1 | 2/2001 | von Oepen | |
| 6,217,608 B1 | 4/2001 | Penn et al. | |
| 6,235,053 B1 | 5/2001 | Jang | |
| 6,261,319 B1 | * 7/2001 | Kveen et al. | 623/1.15 |
| 6,342,067 B1 | 1/2002 | Mathis et al. | |
| 6,527,799 B2 | * 3/2003 | Shanley | 623/1.15 |
| 6,679,910 B1 | * 1/2004 | Granada | 623/1.15 |

FOREIGN PATENT DOCUMENTS

| | | |
|---|---|---|
| EP | 0 662 307 A1 | 12/1995 |
| EP | 0 662 307 B1 | 6/1998 |
| WO | WO 9917680 | 4/1999 |
| WO | WO 00/03862 | 1/2000 |

* cited by examiner

Primary Examiner—David J. Isabella
(74) Attorney, Agent, or Firm—Townsend and Townsend and Crew LLP

(57) ABSTRACT

Luminal prostheses comprise adjacent expansible segments, typically serpentine ring segments joined by sigmoidal links. By properly orienting the sigmoidal links and aligning hinge regions on adjacent serpentine rings, enhanced performance can be obtained.

7 Claims, 7 Drawing Sheets

VASCULAR PROSTHESIS

BACKGROUND OF THE INVENTION

The present invention relates generally to medical devices and methods using the same. More particularly, the present invention relates to the structure of radially expansible luminal prostheses, including stents and grafts.

Luminal prostheses are provided for a variety of medical purposes. For example, luminal stents can be placed in various body lumens, such as blood vessels, the ureter, the urethra, biliary tract, and gastrointestinal tract, for maintaining patency. Luminal stents are particularly useful for placement in pre-dilated atherosclerotic sites in blood vessels. Luminal grafts can be placed in blood vessels to provide support in diseased regions, such as aortic abdominal, and other aneurysms.

Both stent and graft prostheses must meet certain mechanical criteria to function successfully. In particular, such prostheses should be at least partly flexible or articulated (such as rigid sections that articulate relative to one another) over their lengths so that they may be advanced through tortuous body lumens, such as those of the coronary vasculature. In addition, the prostheses should preferably maintain their original length or foreshorten minimally when the prostheses assume an expanded configuration. Further such prostheses must have sufficient mechanical strength, particularly hoop strength, in order to mechanically augment the luminal wall strength and thus assure lumen patency. The ability to meet these requirements is severely limited in the case of cylindrical endoluminal prostheses which are delivered in a radially constrained or collapsed configuration. Such prostheses must radially expand at a target site within the body lumen, so any adaptations which are intended to enhance flexibility will not interfere with the ability to radially expand or to maintain strength once expanded.

Such prostheses, including stents, can suffer from a variety of performance limitations including fishscaling, poor tracking, flaring, and unwanted twisting upon deployment. Fishscaling is a phenomena which occurs when the prosthesis is flexed or articulated during delivery or tracking, resulting in the expanded prosthesis having unwanted outward protrusion of portions of the prosthesis from its surface, thereby increasing the likelihood that the prosthesis will dig into or otherwise engage the wall of the body lumen during delivery and even arrest the progress of the prosthesis and its delivery system to the diseased region (or target site). Poor tracking performance may be exhibited when the prosthesis' ability to pass smoothly through tortuous pathways is below the desired level. Flaring is a phenomena which occurs when the distal or proximal end of the prosthesis are bent outward, assuming a crown-like configuration due to bending forces placed on these elements as the prosthesis passes through tortuous body passageways, often resulting in the same deleterious effects as the previously described fishscaling phenomenon, injuring or traumatizing the blood vessel wall as the prosthesis is delivered or tracked within the blood vessel. A common problem with many of the current devices is their being twisted upon or after deployment in the lumen, resulting in unwanted deformation. The unwanted twisting may occur during the deployment of the device. Often, the devices, when for example deployed by an expandable member such as a balloon, is first expanded at its two ends with the midsection, usually at the center, of the device exhibiting an inward crease with its peak pointing inward in the luminal direction. Such inwardly facing peaks then result in a smaller local inner diameter of the device, leading to obstruction of the lumen.

Accordingly, it would be a significant advance to provide improved devices and methods using the same. This invention satisfies at least some of these and other needs.

BRIEF SUMMARY OF THE INVENTION

The present invention provides improved luminal prostheses suitable for endoluminal placement within body lumens, particularly blood vessels, and most particularly coronary and peripheral arteries. The luminal prostheses may be in the form of stents, intended for maintaining luminal patency, or may be in the form of grafts, intended for protecting or enhancing the strength of a luminal wall. Generally, the term "stent" will be used to denote a vascular or other scaffold structure comprising expansible components, such as ring segments, which when expanded form an open lattice or framework which is disposed against the luminal wall. In contrast, the term "graft" will generally denote such as luminal scaffold which is covered by a liner, membrane, or other permeable or impermeable layer which covers at least a portion of the scaffold. The drawings included herein are generally directed at stent structures, but it will be appreciated that corresponding graft structures could be provided by incorporating a liner, membrane, or the like, on either the outer or inner surfaces of the stent.

The prostheses are preferably placed endoluminally. As used herein, "endoluminally" will mean placement through a body opening or by percutaneous or cutdown procedures, wherein the prosthesis is transluminally advanced through the body lumen from a remote location to a target site in the lumen. In vascular procedures, the prostheses will typically be introduced "endovascularly" using a catheter over a guidewire under fluoroscopic guidance. The catheters and guidewires may be introduced through conventional access sites to the vascular system, such as through the femoral artery, or brachial, subclavian or radial arteries, for access to the coronary arteries.

A luminal prosthesis according to the present invention will usually comprise at least two radially expansible, usually cylindrical, ring segments. Typically, the prostheses will have at least four, and often five, six, seven, eight, ten, or more ring segments. At least some of the ring segments will be adjacent to each other but others may be separated by other non-ring structures.

The luminal prostheses of the present invention are radially expansible. "Radially expansible" as used here in, refers to a prosthesis that can be converted from a small diameter configuration (used for endoluminal placement) to a radially expanded, usually cylindrical, configuration which is achieved when the prosthesis is implanted at the desired target site.

The prosthesis may be minimally resilient, e.g., malleable, thus requiring the application of an internal force to expand and set it at the target site. Typically, the expansive force can be provided by a balloon, such as the balloon of an angioplasty catheter for vascular procedures.

In an embodiment, usually by the application of a radially outward internal force to expand a minimally resilient (usually malleable) prosthesis structure. Such radially outward internal force will usually be provided by an inflatable balloon, and such balloon expansible stents are well-known in the art and described in the background references which have been cited above and are incorporated herein by reference.

Alternatively, at least some of the radially expansible luminal prostheses of the present invention may be self-expanding. By fabricating the prostheses from a resilient material, usually a metal, such as spring stainless steel, a nickel-titanium alloy (such as Nitinol® alloy), or the like, the prosthesis can be designed to have a large (fully expanded) diameter in an unconstrained state. The diameter of the prosthesis can be reduced by applying a radial constraint, e.g., by placing the prosthesis within a sleeve, tube, or other constraining structure. In that way, the self-expanding prosthesis can be delivered while constrained and deployed by releasing the constraint at the target site within the body lumen. The general principles of constructing self-expanding stents and other luminal prostheses are also well-known in the art and described in at least some of the background references which have previously been incorporated herein.

In an embodiment, a radially expansible luminal prosthesis comprises a plurality of unit segments, usually serpentine ring segments, including struts regions connected by hinge regions.

In an embodiment, the hinge regions are usually formed by a short curved, normally a C- or U-shaped region which permits the connected struts to reverse direction in order to define the serpentine ring pattern. In an embodiment, the hinge region includes an apex portion with side potions extending on either side of the apex, the side portions transforming into the strut region of the ring.

In an embodiment at least some, usually all of the hinge regions are radially off set from one another. In another embodiment, at least some, usually all of the hinge regions are radially aligned with one another.

At least some of the longitudinally adjacent serpentine rings are joined by links which may be malleable or elastically deformable in order to allow the adjacent segments to flex relative to each other during prosthesis delivery and expansion.

The links connect at least some of the hinge regions of one ring to at least some of the hinge regions of another ring which is longitudinally offset and adjacent to the one ring. In an embodiment, the connected ring segments are longitudinally immediately adjacent one another, with the connecting links forming a tubular column comprising a plurality of links which are radially offset from one another.

The links can extend from any portion of the hinge region, such as the apex or the side portions, or somewhere in between. In an embodiment, at least some, preferably all, of the links extend laterally from each hinge region, typically from a point where the hinge region transforms into the strut.

In an embodiment, the links generally have a smooth, multi (usually double) curvature shape, usually in a sigmoidal shape, normally an "S" shape. In an embodiment, the links are configured to provide both expansion and contraction between adjacent unit segments.

In an embodiment, a double curvature link includes two curved portions and a straight portion therebetween. In one embodiment, the connecting links within the same connecting link column are oriented in the same direction, the direction being generally different than the direction of an adjacent connecting link column.

In an embodiment, at least some, usually all of the straight portions of links within the same column form an oblique angle, normally either an acute or an obtuse angle with an imaginary longitudinal axis of the prosthesis. In one embodiment, at least some, usually all, of the straight portions of the connecting links of an adjacent column are inclined at a supplementary angle, with the longitudinal axis of the prosthesis, to that of its adjacent connecting column.

Supplementary angle, as used herein, refers to two or more angles which together form a 180 degree angle with an axis.

The use of such sigmoidal links is beneficial since it permits the longitudinal expansion or contraction of the prosthesis to accommodate length changes as the prosthesis is expanded. Such links further permit bending of the prosthesis since they allow differential motion of adjacent serpentine rings. Such flexibility is particularly advantageous since it allows improved tracking of the prosthesis as it is delivered to an endoluminal location. The sigmoidal links also improve the conformability of the expanded prosthesis when placed in a native vessel, artificial graft, or other body lumen location. In the embodiments where the links attach away from the apex of the hinge region, stress at the apex is reduced and uniform expansion of each ring segment is enhanced.

The dimensions of the luminal prosthesis will depend on its intended use. Typically, the prosthesis will have a length in the range from about 1 to 100 mm, usually being from about 8 to 50 mm for vascular applications; and from about 20 to about 200 mm, usually being from about 50 to about 150 mm for non-vascular applications.

The small (radially collapsed) diameter of the cylindrical prostheses will typically be in the range from about 0.25 to about 20 mm, usually being from about 0.4 to about 15 mm, and normally from about 0.8 to about 10 mm.

The small (radially collapsed) diameter of cylindrical prostheses for vascular applications typically range from about 0.25 to about 1.5 mm for coronary and from about 1 to about 4 mm for peripheral applications, usually from about 0.4 to about 1.25 mm for coronary and from about 1.5 to about 3 mm for peripheral applications, and normally from about 0.8 to about 1.2 mm for coronary and from about 1.75 to about 2.5 mm for peripheral applications.

For nonvascular applications, the prosthesis will typically have a small diameter ranging from about 1.5 to about 20 mm, usually from about 2 to about 15 mm, and normally from about 5 mm to about 10 mm.

The large (radially enlarged) diameter of the cylindrical prostheses will typically be in the range from about 1 mm to about 100 mm, usually being from about 1.5 mm to about 75 mm, and normally from about 2 to about 50 mm.

The large (radially enlarged) diameter of cylindrical prostheses for vascular applications typically range from about 1 mm to about 7 mm for coronary and from about 1 mm to about 30 mm for peripheral applications, usually from about 1.5 mm to about 5 mm for coronary and from about 3 mm to about 25 mm for peripheral applications, and normally from about 2 mm to about 4 mm for coronary and from about 5 mm to about 20 mm for peripheral applications.

For nonvascular applications, the prosthesis will typically have a larger diameter ranging from about 1 mm to about 100 mm, usually from about 5 mm to about 75 mm, and normally from about 10 mm to about 50 mm.

DETAILED DESCRIPTION OF THE INVENTION

Figure 1:
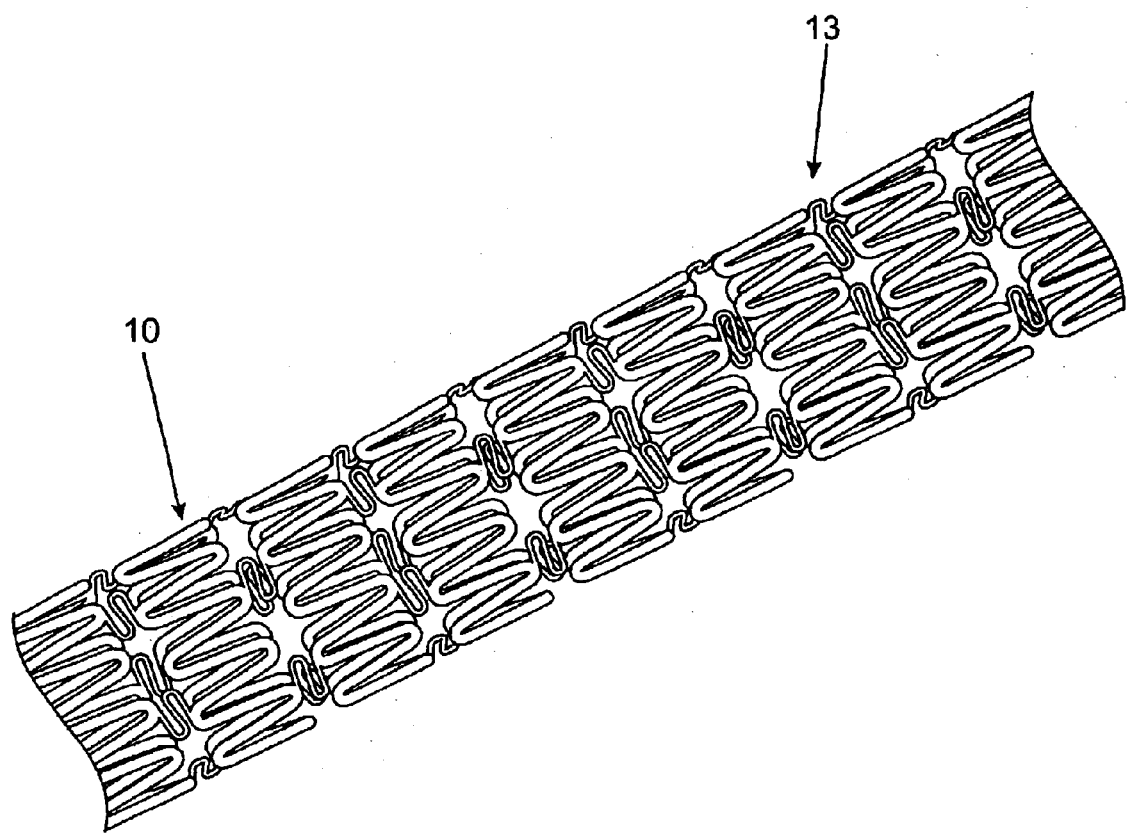
FIG. 1 is a schematic representation of an exemplary prosthesis embodying features of the present invention in unexpanded configurations.

FIG. 1 illustrates a radially expansible luminal prosthesis 10, such as a stent, generally embodying features of the present invention, and including a frame 13 formed from a plurality of radially expansible ring segments 16. Although the final shape of the prosthesis 10 will generally be cylindrical, it should be appreciated that the prosthesis may also be conformable to non-cylindrical cross-sectional lumens and may also be conformable to transversely curved lumens.

An exemplary luminal prosthesis 10 particularly intended for implantation in the vasculature (e.g., coronary or peripheral) comprises from 4 to 50 ring segments 16 (with 7 being illustrated), the segments being joined to a longitudinally set apart adjacent ring segment by at least one link, such as sigmoidal link 19.

Now referring to FIGS. 2A through 2D, the ring segments 16, comprise a plurality of struts 22, normally linear struts, joined by hinge regions 25. As shown, the hinge regions 25 have a curved shape and include an apex portion 28 with side potions 31 extending on either side of the apex and transforming into the strut 22, and trough region 34 opposite the apex 28.

The links 19, connect proximate hinge regions, such as 25A and 25B, of adjacent rings, such as 16A and 16B. The links connecting adjacent ring segments, as for example 16A and 16B, form a radial column 37. The connecting links 19 generally have a smooth, multi (usually double) curvature shape, usually in a sigmoidal shape, normally an "S" shape.

Figure 2A:
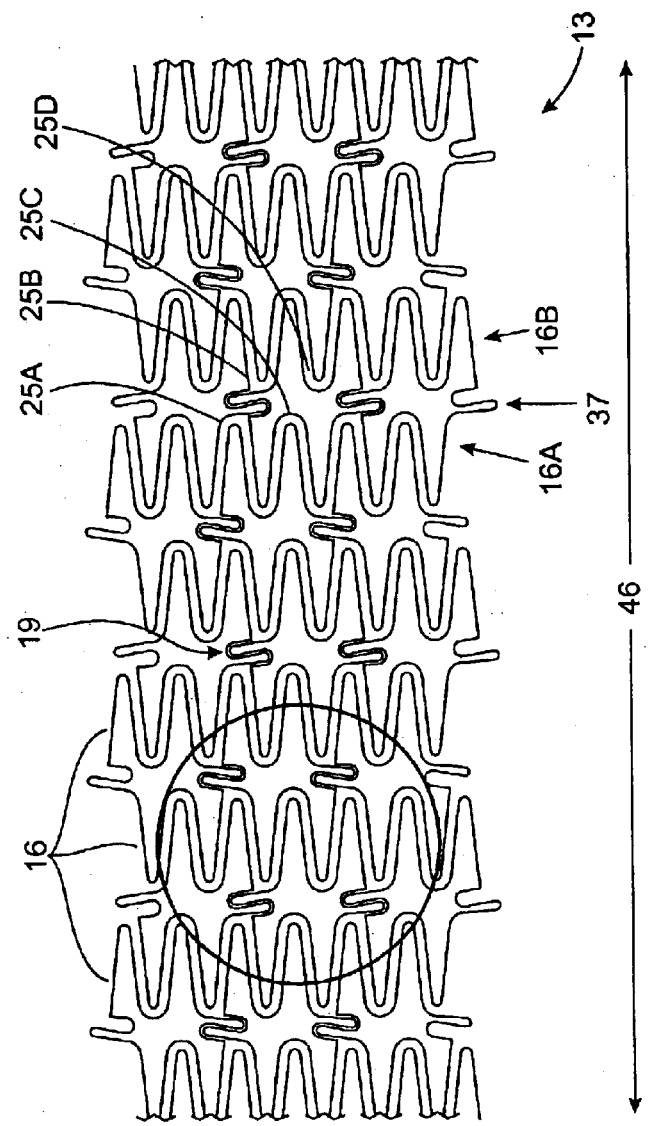
FIGS. 2A and 2B are "rolled out" views of an exemplary embodiment of the prosthesis of FIG. 1.

The links 19 extend from some of the radial hinge regions within the same ring segment 16, such that not all hinge regions of a ring segment are connected to hinge regions of an adjacent ring, although embodiments connecting all of the proximate hinge regions, or other configurations, are within the scope of the present invention. By way of example, as shown in FIG. 2A, ring segment 16A and 16B, comprise hinge regions 25A and 25B which are connected to one another by way of link 19, and hinge regions 25C and 25D, which are free from connections to a hinge region on an adjacent ring. The connected hinge regions may alternate with non-connected hinge regions or may have certain repeat patterns. As shown in FIG. 2C, the connected and non-connected hinge regions alternate in the mid-section of the prosthesis with the most distal two link columns at both ends of the prosthesis emerging in a pattern of 3 connected hinge regions followed by a non-connected hinge region.

Figure 2B:
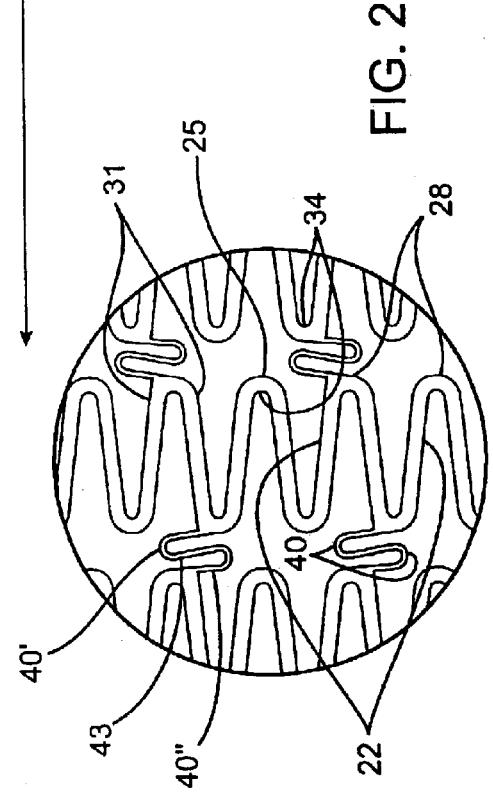
Figure 2C:
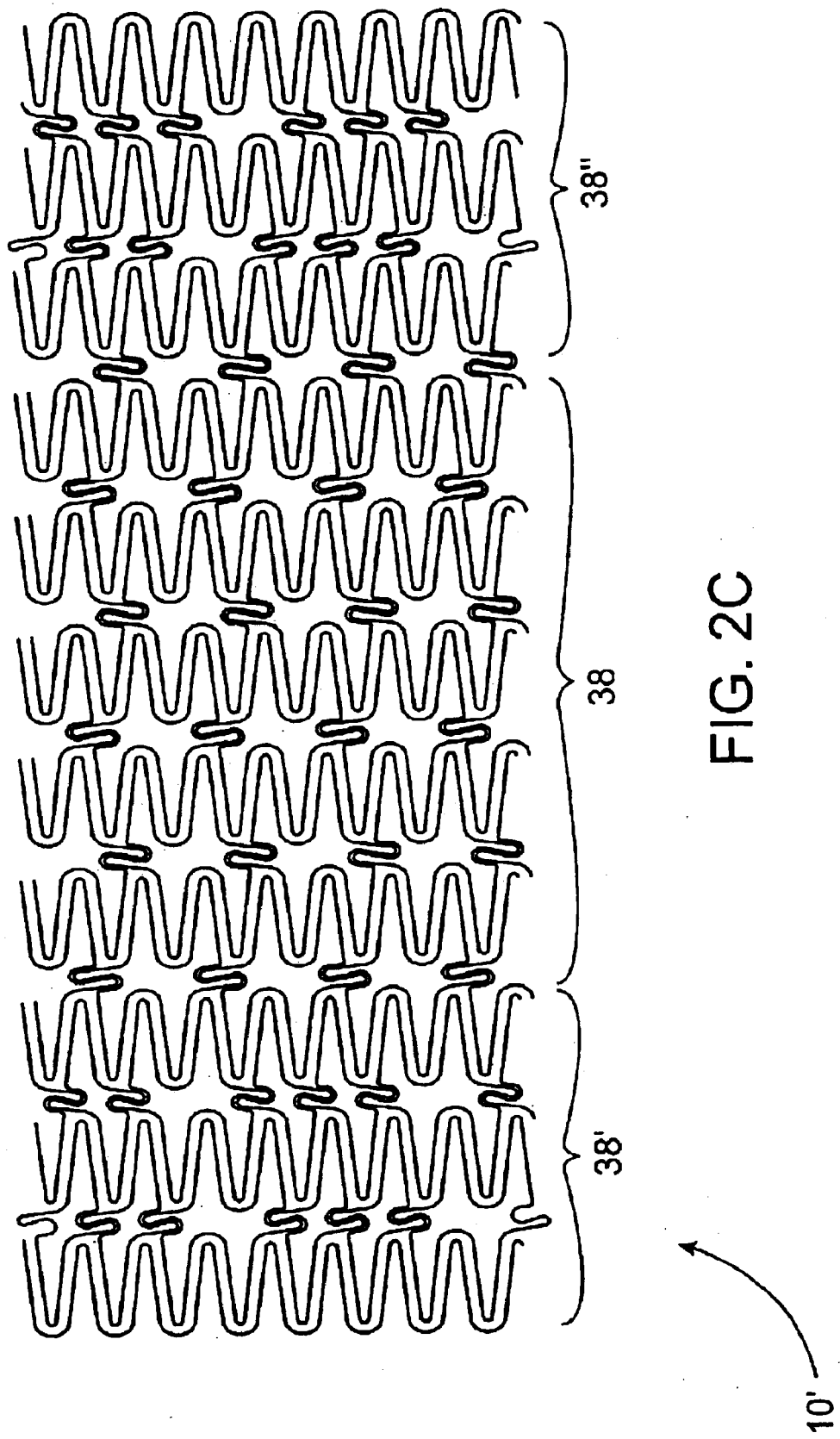
FIGS. 2C and 2D are "rolled out" views of an exemplary embodiment of the prosthesis of FIG. 1, in unexpanded and expanded configurations, respectively.
Figure 2D:
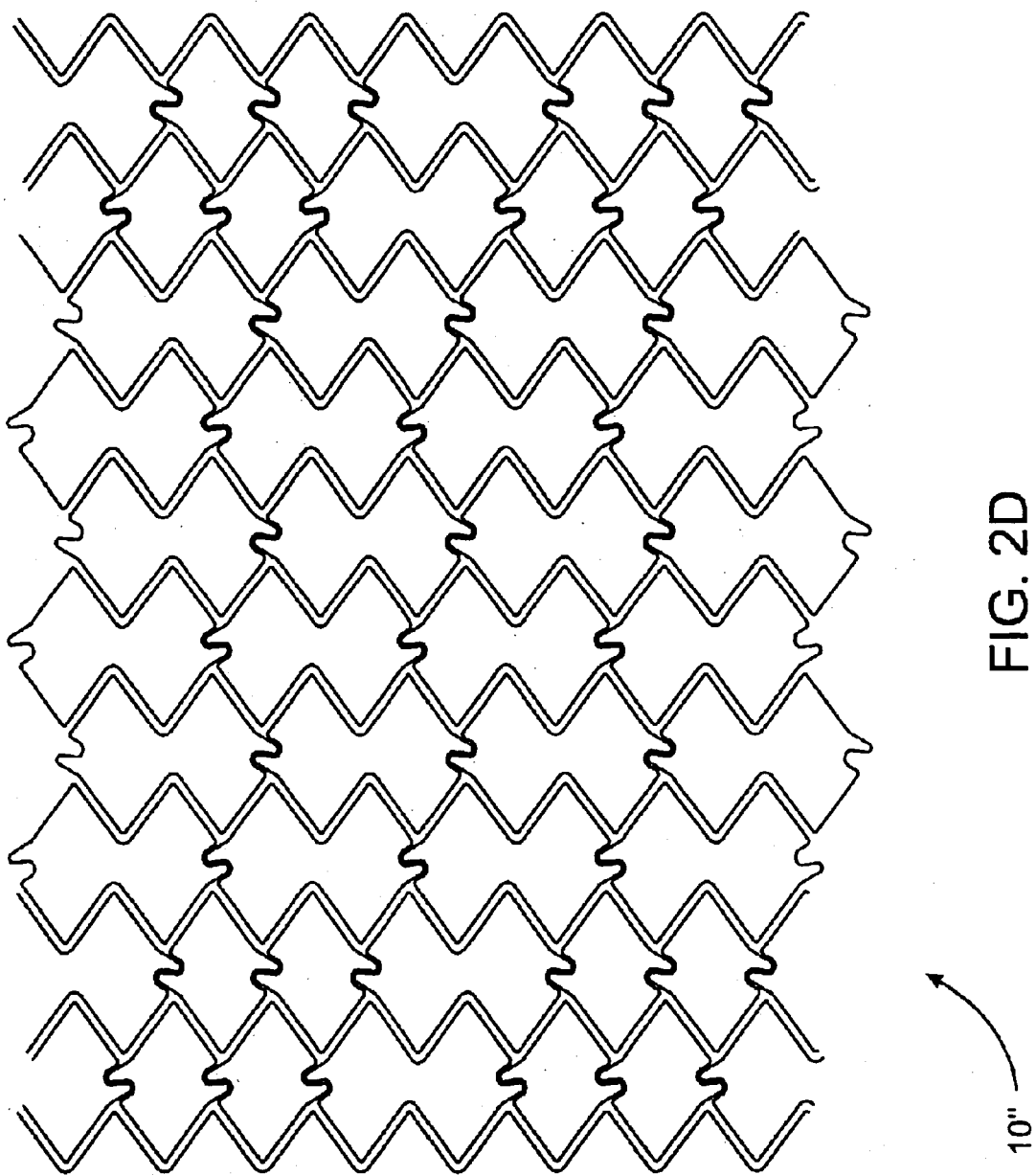

Now referring back to FIG. 2A and its enlarged view FIG. 2B, the double curvature links 19 include two curved portions, 40, such as 40' and 40", and a straight portion 43 disposed therebetween. The connecting links 19 within the same connecting link column 37 are oriented in the same direction with the straight portion 43 of at least some of the links form an oblique angle with an imaginary longitudinal axis 46 of the frame 13.

By way of example, the straight portion of the links of two adjacent columns may form similar type of angles with the longitudinal axis, e.g., obtuse or acute. Furthermore, the angles within the same column, even when generally either obtuse or acute, may be similar or different than another angle within the same column.

Figure 3:
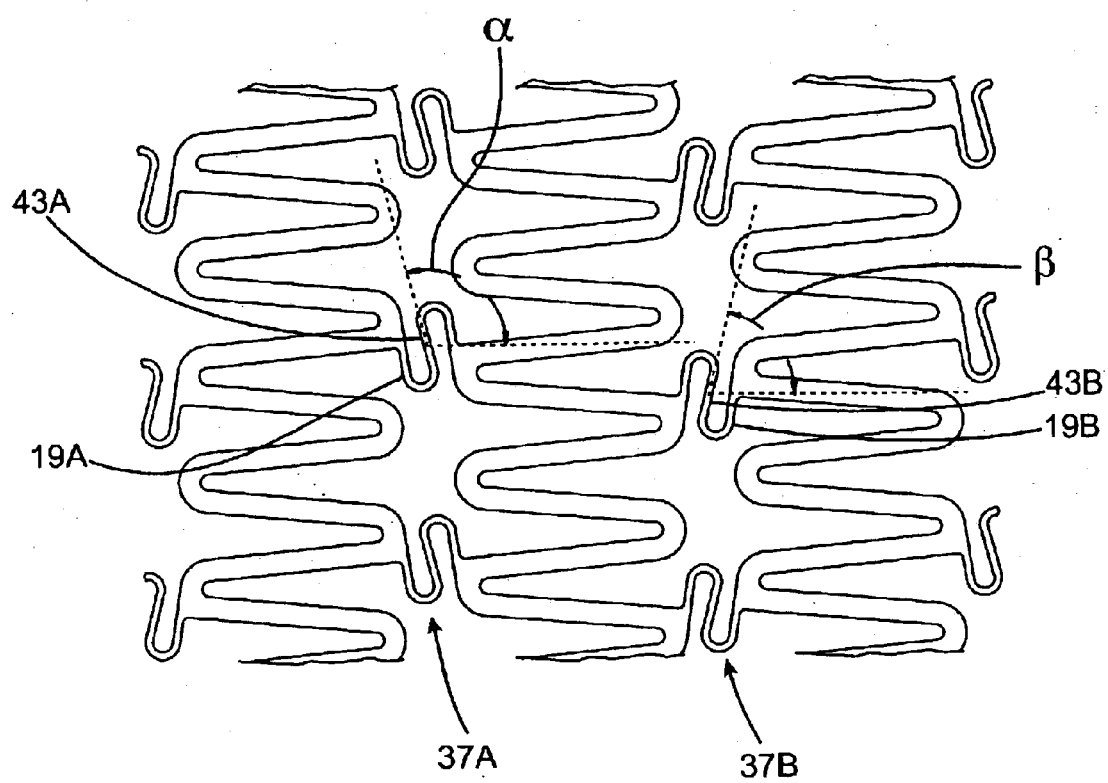
FIG. 3 is a partial "rolled out" view of structure of FIG. 2A with the straight portion of the links forming oblique angles with a longitudinal axis of the prosthesis.

As further shown in FIG. 3, the straight portion 43A of the connecting links 19A in one column 37A forms an obtuse angle α with the imaginary longitudinal axis 46 of the frame 13. The obtuse angle α within each column, independently, ranges from about 95 to about 170, usually from about 100 to about 135, and normally from about 105 to about 130 degrees.

The straight portion 43B of the connecting links 19B of a column 37B adjacent to column 37A, forms an acute, angle β with the longitudinal axis 46. The acute angle β within each column, independently, ranges from about 10 to about 85, usually from about 45 to about 80 and normally from about 50 to about 75 degrees.

The obtuse and acute angles, α and β, of adjacent rings, preferably, together, form supplementary angles with the longitudinal axis 46.

In one embodiment, links 19 have similar dimensions (e.g., the length of the straight portion 43A is similar, usually the same, as the length of the straight portion 43B) such that links in adjacent columns are mirror images one another.

Although the prosthesis as shown includes an even number of connecting columns 37 with the straight portion of the alternating columns forming either obtuse or acute angles, the invention is not limited to such alternating pattern and other configurations and patterns are within the scope of the present invention.

Figure 4A:
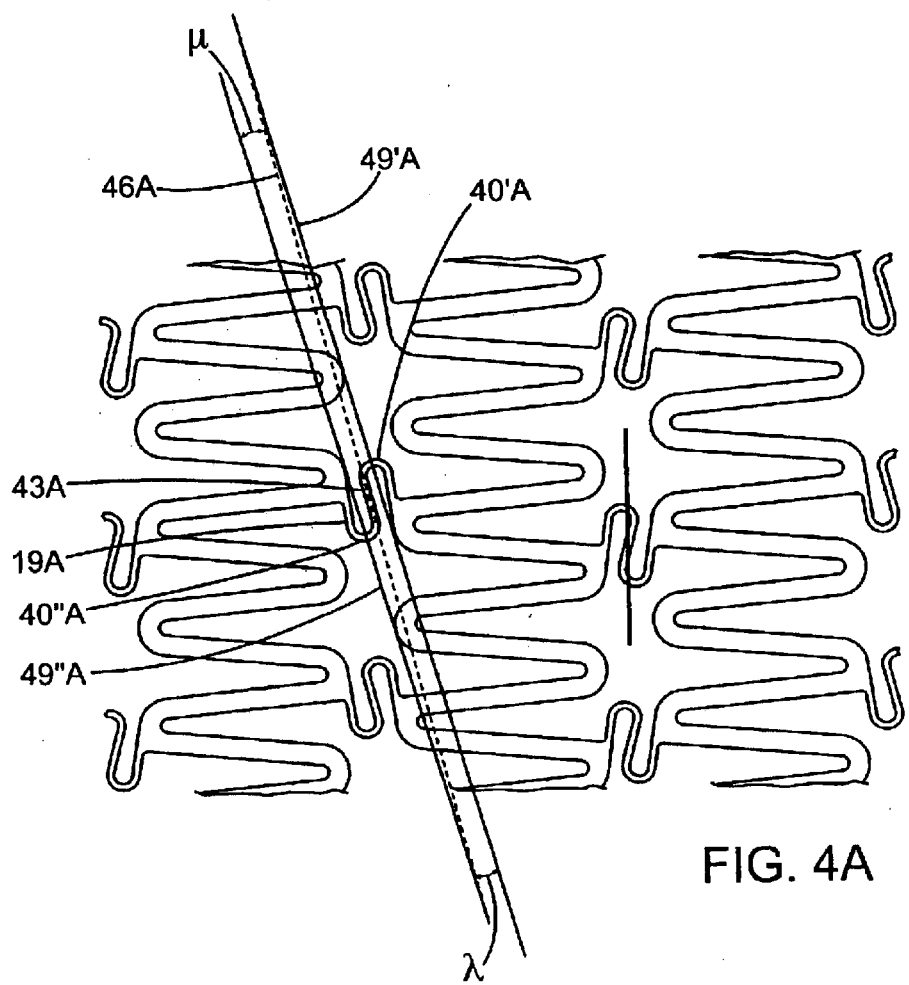
FIG. 4A is a partial "rolled out" view of an embodiment of the structure in FIG. 2A showing a straight portion of the hinge portions intersecting the imaginary lines bisecting the curved portions of the links.

As can be seen in FIG. 4A, in one embodiment, curved portions 40'A and 40"A of the multi-curvature link 19, project in opposite directions such that an imaginary axis 46A of the straight portion 43A, at each end intersects one imaginary line which bisects one of the curved portions. As shown, imaginary lines 49'A and 49"A, each bisects the curved portions, 40'A and 40"A, respectively. The intersection of the axis 46"A of the straight portion with imaginary lines 49'A and 49"A, respectively, forms angles λ and μ, respectively. It should be appreciated that although the intersection of the bisecting lines with the imaginary axis of the straight portion has been described with respect to one link column such as one forming obtuse angle with the longitudinal axis of the prosthesis, intersections may also be formed in adjacent columns which form acute angles with the longitudinal axis of the prosthesis.

Figure 4B:
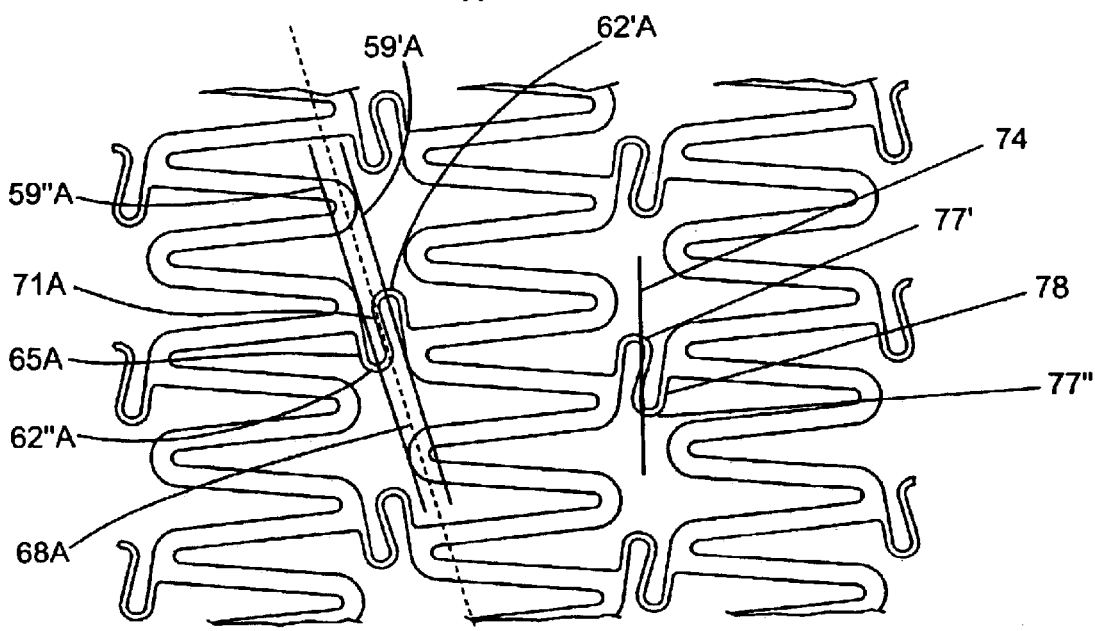
FIG. 4B is a partial "rolled out" view of an embodiment of the structure in FIG. 2A showing a straight portion of the hinge portions being parallel to imaginary bisecting the curved portions of the links.

As further can be seen in FIG. 4B, in one embodiment, imaginary lines 59'A and 59"A bisecting the curved portions 62'A and 62"A, respectively, of a link 65A, are parallel with the axis 68A of the straight portion 71A.

In one embodiment, features of which are also shown in FIG. 4B, there is at least one radial plane 74 that intersects both curved portions, 77' and 77", of a given link, 78. It should be appreciated that this feature may be present independent of the other features previously discussed with reference to FIGS. 4A and 4B.

Figure 5A:
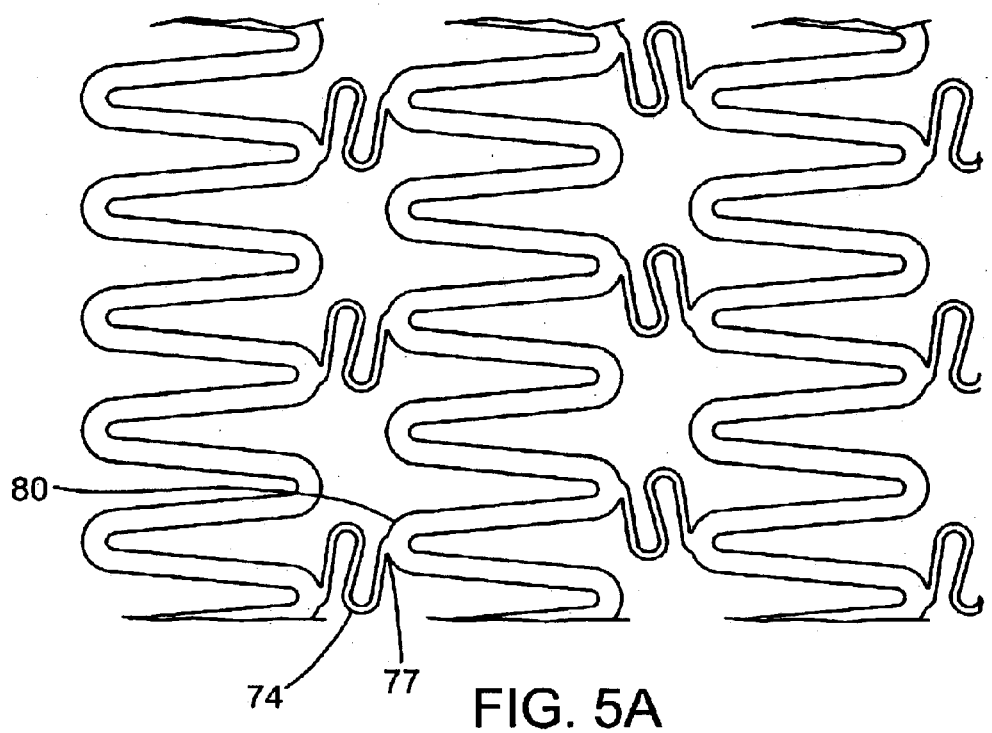
FIG. 5A is a partial "rolled out" view of an alternate embodiment of the structure of FIG. 2A with the links emerging from the apices.

Now referring to FIG. 5A, in an alternate embodiment, the links 74 generally emerge from apex portion 77 of hinge region 80, as compared to the side portions described earlier in reference to FIG. 2.

Figure 5B:
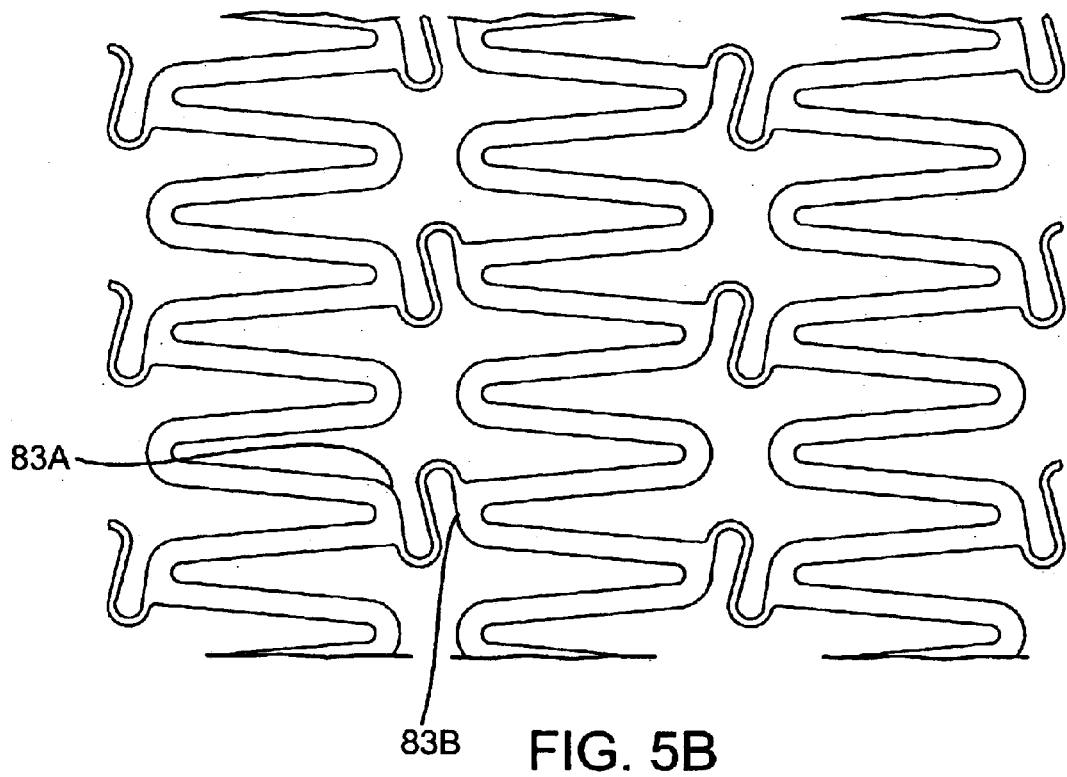
FIG. 5B is a partial "rolled out" view of an alternate embodiment of the structure of FIG. 3 with the hinge regions of the longitudinally adjacent rings being radially aligned with one another.

In one alternate embodiment, features of which are shown in FIG. 5B, the connected hinge regions, such as hinge regions 83A and 83B are radially aligned with one another, as compared to the radially offset hinge regions in FIG. 2.

In operation, the prosthesis of the present invention, may be placed on an expandable portion of a balloon catheter, or within the lumen of a delivery catheter, and delivered to a desired luminal site and disposed therein, as is known in the art.

Although certain preferred embodiments and methods have been disclosed herein, it will be apparent from the foregoing disclosure to those skilled in the art that variations and modifications of such embodiments and methods may be made without departing from the true spirit and scope of the invention. Therefore, the above description should not be taken as limiting the scope of the invention which is defined by the appended claims.

What is claimed is:

1. A radially expansible luminal prosthesis comprising:
   a plurality of serpentine ring segments including struts and hinge regions disposed therebetween;
   multi-curvature links including two curved portions and at least one straight portion disposed therebetween which forms an oblique angle with an imaginary longitudinal axis of the prosthesis, the links connecting at least some of the hinge regions on adjacent serpentine rings, wherein the links connecting immediate adjacent rings form a radial column with the straight portion of all of the links of the same radial column either forming an acute or obtuse angle with the longitudinal axis of the prosthesis, and wherein for all of the links of the same radial column there is at least one imaginary radial plane that intersects all of the curved portions.

2. The prosthesis of claim 1 wherein all the angles of the same radial column are substantially similar.

3. The prosthesis of claim 2, wherein the angle of one radial column is supplementary to the angle of an adjacent radial column.

4. The prosthesis of claim 2, wherein the radial links of adjacent radial columns are mirror images of one another.

5. The prosthesis of claim 1, wherein the multi-curvature link includes two curved portions projecting in opposite directions from one another with the straight portion disposed therebetween, with an imaginary axis of the straight portion at each end forming an imaginary angle with one imaginary line bisecting one of the curved portions.

6. The prosthesis of claim 1, wherein the multi-curvature link includes two curved portions with the straight portion disposed therebetween, with the curved portions projecting in opposite direction such that an imaginary axis of the straight portion at each end forms an imaginary angle with one imaginary line bisecting one of the curved portions.

7. The prosthesis of claim 6 wherein the angles formed by each of the bisecting lines are substantially similar in value.

\* \* \* \* \*